US011562226B2

(12) United States Patent
Saito

(10) Patent No.: US 11,562,226 B2
(45) Date of Patent: Jan. 24, 2023

(54) COMPUTER-READABLE RECORDING MEDIUM, LEARNING METHOD, AND LEARNING APPARATUS

(71) Applicant: FUJITSU LIMITED, Kawasaki (JP)

(72) Inventor: Takahiro Saito, Asaka (JP)

(73) Assignee: FUJITSU LIMITED, Kawasaki (JP)

( * ) Notice: Subject to any disclaimer, the term of this patent is extended or adjusted under 35 U.S.C. 154(b) by 1043 days.

(21) Appl. No.: 16/251,130

(22) Filed: Jan. 18, 2019

(65) Prior Publication Data

US 2019/0228304 A1 Jul. 25, 2019

(30) Foreign Application Priority Data

Jan. 19, 2018 (JP) .............................. JP2018-007543

(51) Int. Cl.
*G06N 3/08* (2006.01)
*G06F 16/901* (2019.01)
*G16C 20/90* (2019.01)
*G16C 20/70* (2019.01)

(52) U.S. Cl.
CPC ........... *G06N 3/08* (2013.01); *G06F 16/9024* (2019.01); *G16C 20/70* (2019.02); *G16C 20/90* (2019.02)

(58) Field of Classification Search
CPC .............................. G06N 3/08; G06F 16/9024
See application file for complete search history.

(56) References Cited

U.S. PATENT DOCUMENTS

| 2004/0088118 A1* | 5/2004 | Jensen | G16C 20/80 702/30 |
| 2019/0139622 A1* | 5/2019 | Osthege | G06N 3/084 |
| 2021/0241858 A1* | 8/2021 | Kurita | G16C 20/30 |
| 2021/0248507 A1* | 8/2021 | Jippo | G06F 17/11 |

FOREIGN PATENT DOCUMENTS

| JP | 2014-059754 | 4/2014 | |
| JP | 2015-204084 | 11/2015 | |
| JP | 2016-207072 | 12/2016 | |
| JP | 2017-129995 | 7/2017 | |
| WO | WO-2021038420 A1 * | 3/2021 | ........... C07D 231/56 |
| WO | WO-2021165887 A1 * | 8/2021 | |

OTHER PUBLICATIONS

Koji Maruhashi, "Deep Tensor: Eliciting New Insights from Graph Data that Express Relationships between People and Things" Fujitsu Sci. Tech. J., vol. 53, No. 5, (Sep. 2017), pp. 26-31 (6 pages).

* cited by examiner

*Primary Examiner* — Shirley X Zhang
(74) *Attorney, Agent, or Firm* — Fujitsu Patent Center

(57) ABSTRACT

A non-transitory computer-readable recording medium stores a learning program that causes a computer to execute a machine learning process for graph data. The machine learning process includes: generating, from graph data to be subjected to learning, extended graph data where at least some of nodes included in the graph data have a value of the nodes and a value corresponding to presence or absence of an indefinite element at the nodes; and obtaining input tensor data by performing tensor decomposition of the generated extended graph data, performing deep learning with a neural network by inputting the input tensor data into the neural network upon deep learning, and learning a method of the tensor decomposition.

3 Claims, 6 Drawing Sheets

COMPUTER-READABLE RECORDING MEDIUM, LEARNING METHOD, AND LEARNING APPARATUS

CROSS-REFERENCE TO RELATED APPLICATION

This application is based upon and claims the benefit of priority of the prior Japanese Patent Application No. 2018-007543, filed on Jan. 19, 2018, the entire contents of which are incorporated herein by reference.

FIELD

The embodiment discussed herein is related to a learning program, a learning method, and a learning apparatus.

BACKGROUND

A graph structure learning technique that enables deep learning of data on a graph structure (hereinafter, one form of an apparatus that performs such graph structure learning being referred to as "Deep Tensor") has been known. In learning by Deep Tensor, a partial structure contributing to discrimination is able to be extracted automatically from graph structures that have been input.

[Patent Literature 1] Japanese Laid-open Patent Publication No. 2016-207072
[Patent Literature 2] Japanese Laid-open Patent Publication No. 2014-059754
[Patent Literature 3] Japanese Laid-open Patent Publication No. 2017-129995
[Patent Literature 4] Japanese Laid-open Patent Publication No. 2015-204084
[Non-patent Literature 1] "Deep Tensor: Eliciting New Insights from Graph Data that Express Relationships between People and Things", Koji Maruhashi, Fujitsu Sci. Tech. J., Vol. 53, No. 5, pp. 26-31 (September 2017)

In machine learning technology, selection from two learning patterns is possible, the two learning patterns being: learning (learning with labels) in consideration of values of nodes (node labels) forming a graph serving as an input; and learning (learning without labels) not in consideration of the node labels. For example, for data of a graph structure representing connections between chemical elements of a chemical compound, learning in consideration of types of the chemical elements corresponding to nodes is desirable. However, one may like a discriminant rule in a discriminant model (a learning model) of deep learning to allow a specific node among nodes of data of a graph structure to be indefinite.

However, Deep Tensor is not equipped with a learning pattern not in consideration of labels for some of nodes in a graph that has been input. Thus, even if an element of a specific node is allowed to be indefinite under a true discriminant rule, data corresponding to an element not included in training data are difficult to be discriminated correctly.

For example, a situation is now be supposed, where in a discriminant problem: when a specific partial structure is present in a graph structure serving as an input, a TRUE determination is able to be made correctly; when the specific partial structure is not present in the graph structure, a FALSE determination is able to be made correctly; a label related to one specific node in the partial structure is indefinite; and labels related to the other nodes are definite.

If learning with labels is performed in this situation, in spite of the label for the one specific node being allowed to be indefinite, the learning with labels will be constrained by the labels of the other nodes in the learning data, and a FALSE determination will be made when a label that is not in the learning data has been assigned to the one specific node, resulting in determination error.

Further, if learning without labels is performed in the above situation, since a partial structure assigned with another label will match a node having a definite label in the partial structure, a TRUE determination will be made, resulting in determination error.

SUMMARY

According to an aspect of an embodiment, a non-transitory computer-readable recording medium stores a learning program that causes a computer to execute a machine learning process for graph data. The machine learning process includes: generating, from graph data to be subjected to learning, extended graph data where at least some of nodes included in the graph data have a value of the nodes and a value corresponding to presence or absence of an indefinite element at the nodes; and obtaining input tensor data by performing tensor decomposition of the generated extended graph data, performing deep learning with a neural network by inputting the input tensor data into the neural network upon deep learning, and learning a method of the tensor decomposition.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Preferred embodiments of the present invention will be explained with reference to accompanying drawings. The disclosed techniques are not limited by these embodiments. Further, the following embodiments may be combined as appropriate so long as no contradictions arise therefrom.

Figure 1:
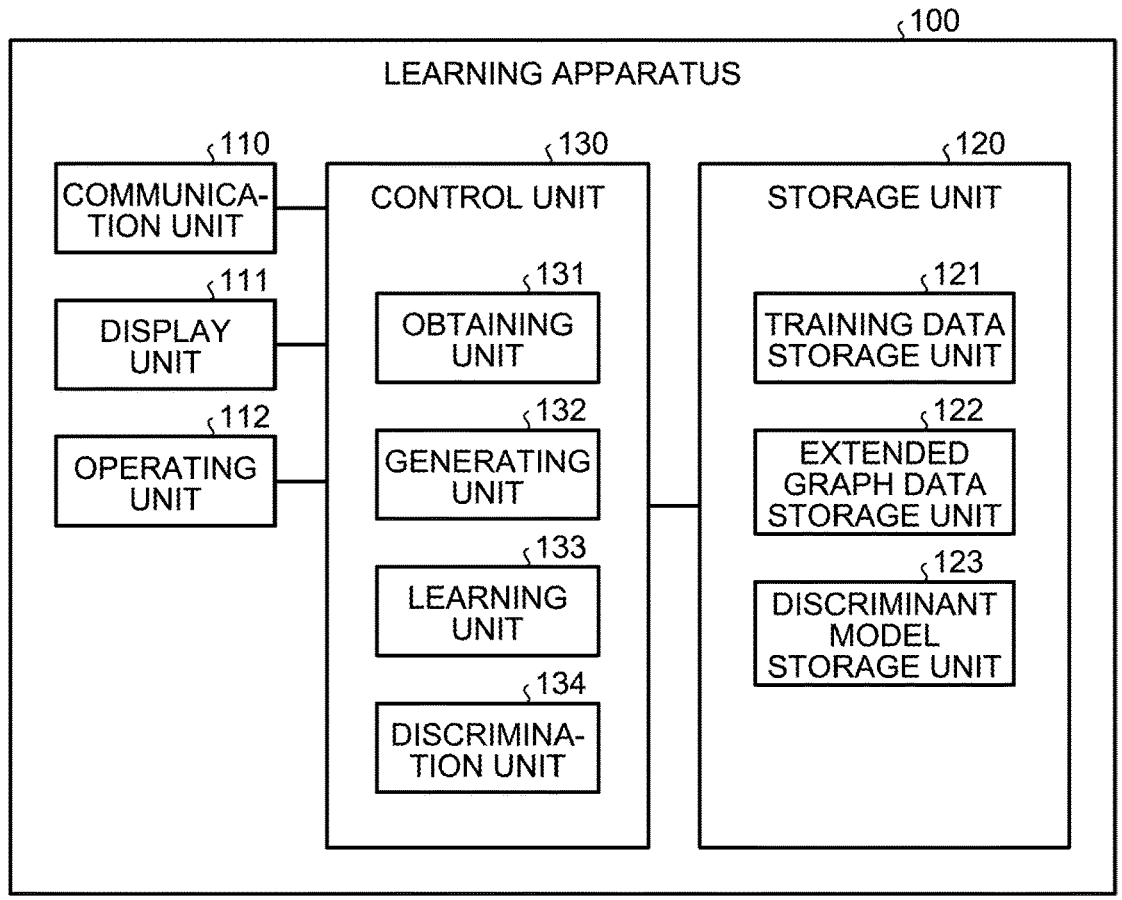
FIG. 1 is a block diagram illustrating an example of a configuration of a learning apparatus according to an embodiment.

FIG. 1 is a block diagram illustrating an example of a configuration of a learning apparatus according to an embodiment. A learning apparatus 100 illustrated in FIG. 1 is an example of a learning apparatus that generates a discriminant model by Deep Tensor for deep learning with data of graph structures, and discriminates data of a new graph structure by using the discriminant model. The learning apparatus 100 generates, from graph data to be subjected to learning, extended graph data where at least some of nodes included in the graph data have a value of the nodes and a value corresponding to presence or absence of an indefinite element at the nodes. The learning apparatus 100 performs tensor decomposition of the generated extended graph data serving as input tensor data, performs deep learning with a neural network by input of the decomposed data into the neural network upon deep learning, and learns a method of the tensor decomposition. Thereby, the learning apparatus 100 enables improvement in the discrimination accuracy of machine learning for a graph including an indefinite element in the discriminant rule.

Firstly, Deep Tensor will be described. Deep Tensor is deep learning having tensors (graph information) serving as inputs, and enables learning with a neural network and automatic extraction of a partial graph structure contributing to discrimination. Processing of this extraction is realized by the learning with the neural network, and learning of parameters of tensor decomposition of input tensor data.

Figure 2:
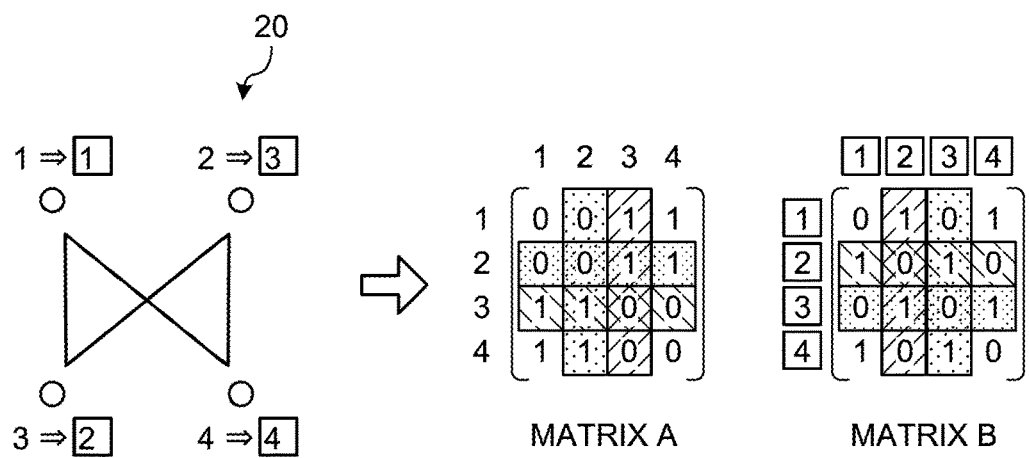
FIG. 2 is a diagram illustrating an example of relation between a graph structure and tensors.

Next, by use of FIG. 2 and FIG. 3, graph structures will be described by use of FIG. 2 and FIG. 3. FIG. 2 is a diagram illustrating an example of relation between a graph structure and tensors. A graph 20 illustrated in FIG. 2 has four nodes joined by edges each representing a relation between nodes (for example, "having a correlation coefficient equal to or larger than a predetermined value"). Nodes that are not joined by an edge do not have the relation. When the graph 20 is represented by a second-order tensor, that is, a matrix, for example, a matrix representation based on numbers on the left side of the nodes is represented by a "matrix A", and a matrix representation based on numbers on the right side of the nodes (the numbers surrounded by enclosure lines) is represented by a "matrix B". Each component of these matrices is represented by "1" when the nodes have been joined (connected), and represented by "0" when the nodes have not been joined (connected). In the following description, such a matrix will also be referred to as an incidence matrix. The "matrix B" is able to be generated by simultaneous substitution of second and third rows of the "matrix A" with each other and second and third columns of the "matrix A" with each other. In Deep Tensor, by use of such a substitution process, processing is performed in disregard of difference in order. That is, in Deep Tensor, ordering in the "matrix A" and "matrix B" is ignored and the "matrix A" and "matrix B" are treated as the same graphs. Similar processing is performed for third or higher order tensors.

Figure 3:
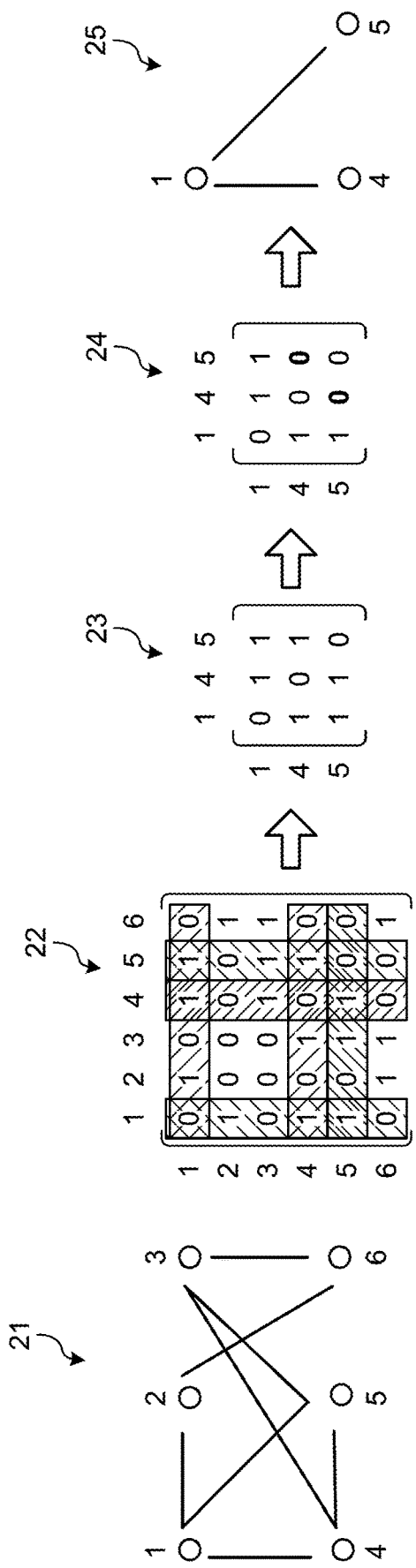
FIG. 3 is a diagram illustrating an example of extraction of a partial graph structure.

FIG. 3 is a diagram illustrating an example of extraction of a partial graph structure. A graph 21 illustrated in FIG. 3 has six nodes joined by edges. The graph 21 is able to be represented by a matrix 22 when represented by a matrix (tensor). By a combination of calculation for exchange between specific rows and between specific columns, calculation for extraction of specific rows and columns, and calculation for substitution of a non-zero element in an incidence matrix with a zero, on the matrix 22; a partial graph structure is able to be extracted. For example, a matrix corresponding to "nodes 1, 4, and 5" of the matrix 22 is extracted as a matrix 23. Subsequently, substitution of values between "nodes 4 and 5" of the matrix 23 with zeros results in a matrix 24. A graph 25 is obtained as a partial graph structure corresponding to the matrix 24.

Such an extraction process for a partial graph structure is realized by mathematical calculation called tensor decomposition. Tensor decomposition is calculation for approximation of an input n-th order tensor by a product of an n-th or lower order tensor. For example, an input n-th order tensor is approximated by a product of one n-th order tensor (called a core tensor), and n tensors of a lower order (when n>2, normally a 2nd order tensor, that is, a matrix, being used). This decomposition is not unique, and an arbitrary partial graph structure in the graph structure represented by the input data may be included in the core tensor.

Next, problems in extraction of a partial graph structures will be described. In Deep Tensor, learning and discrimination are performed with graph structure data (a tensor) of input data being regarded as either a graph without labels or a graph with labels. Which one of these graphs the input data are regarded as in the processing is set by a user. In the following description, a case where input data are regarded as a graph without labels will be referred to as a graph processing mode without labels and a case where input data are regarded as a graph with labels will be referred to as a graph processing mode with labels.

Examples of a task where the graph processing mode without labels is appropriate include unauthorized access detection. For example, for detection of unauthorized access using communication information between personal computers (PCs) on a network, defining nodes of a graph as PCs, and defining labels of these nodes as internet protocol (IP) addresses of these PCs may be considered. However, when a partial graph structure with labels (a core tensor) is learnt with such a graph with labels serving as an input, since the IP addresses do not overlap at all with those in another network, there will be no match. Therefore, for unauthorized access detection, learning is desired to be performed with input data that are graphs without labels.

On the other hand, examples of a task where the graph processing mode with labels is appropriate include drug efficacy determination. For example, when whether or not specific drug efficacy is available is determined with a graph representing a structure of a chemical compound serving as an input, what kind of chemical elements are bonded in what way is important. Therefore, for drug efficacy determination, learning is desired to be performed with input data that are graphs with labels having names of chemical elements as labels.

For drug efficacy determination, for example, in some cases, chemical elements of some of nodes in a graph representing a structure of a chemical compound may be indefinite. In such a case, a generalized discriminant rule where some of nodes of a partial graph structure are indefinite elements is desired to be able to be learnt as a discriminant rule. For example, it is now supposed that new data are discriminated based on whether or not the new data have a common feature that partial graph structures contributing to discrimination have in common among positive examples of training data. However, in Deep Tensor where simply data of a graph structure serve as an input, when partial graph structures having a common feature have indefinite elements at some of their nodes, this common feature is difficult to be learnt.

Figure 4:
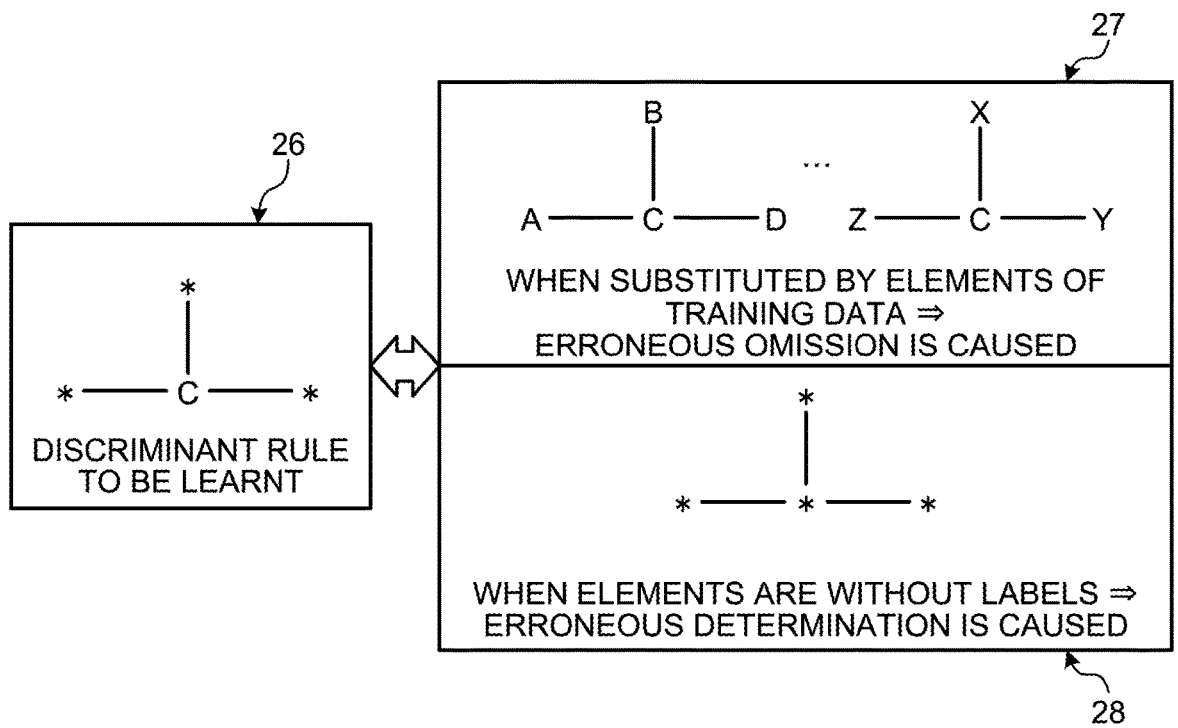
FIG. 4 is a diagram illustrating an example of problems in extraction of partial graph structures.

FIG. 4 is a diagram illustrating an example of problems in extraction of partial graph structures. A graph 26 illustrated in FIG. 4 is a partial graph structure representing a discriminant rule desired to be learnt. In the graph 26, a node having an indefinite element is represented as a wild card node (an asterisk, "*"). That is, the graph 26 is a discriminant rule defining that "a node having a label C is connected to three or more nodes having arbitrary labels (nodes having indefinite elements)".

On the other hand, graphs 27 are partial graph structures extracted when the graph processing mode with labels is used. In this case, learning is performed with the wild card nodes in the graph 26 being substituted by elements (A, B, D, . . . , X, Y, and Z) of training data, but new data matching the graph 26 that is the true discriminant rule may be overlooked. Further, a graph 28 is a partial graph structure extracted when the graph processing mode without labels is used. In this case, all of nodes of the graph 28 are elements without labels, that is, wild card nodes, and thus even new data having a hub node, which corresponds to the node having the label C in the graph 26 and has a label other than the label C, may be erroneously determined as matching.

That is, in the graph processing mode with labels, since the partial graph structure is learnt by use of the labels of all of the nodes as-is, substitution of some of the nodes with wild card nodes is unable to be performed, and a partial graph structure like the graph 26 is unable to be learnt. Further, in the graph processing mode without labels, since the partial graph structure, in which the labels of all of the nodes are arbitrary, that is, wild card nodes, is learnt, a partial graph structure, in which a part of its nodes has a specific label, like the graph 26, is unable to be learnt. Furthermore, in Deep Tensor, existence of both the graph processing mode with labels and the graph processing mode without labels is not supported. In contrast, according to this embodiment, by addition of a graph formed of wild card nodes corresponding to a graph of input data, discrimination accuracy of machine learning for a graph including an indefinite element in a discriminant rule is able to be improved.

Next, a configuration of the learning apparatus 100 will be described. As illustrated in FIG. 1, the learning apparatus 100 has a communication unit 110, a display unit 111, an operating unit 112, a storage unit 120, and a control unit 130. The learning apparatus 100 may have, in addition to the functional units illustrated in FIG. 1, various functional units that a known computer has, for example, functional units, such as various input devices and a sound output device.

The communication unit 110 is realized by, for example, a network interface card (NIC). The communication unit 110 is a communication interface, which is connected to another information processing apparatus via a network not illustrated in the drawings, wiredly or wirelessly, and controls communication of information with the information processing apparatus. The communication unit 110 receives training data for learning and new data to be discriminated, from, for example, a terminal of an administrator. Further, the communication unit 110 transmits a result of the learning and a result of the discrimination, to the terminal of the administrator.

The display unit 111 is a display device for displaying thereon various kinds of information. The display unit 111 is realized by, for example, a liquid crystal display serving as the display device. The display unit 111 displays thereon various screens, such as display screens input from the control unit 130.

The operating unit 112 is an input device that receives various operations from a user of the learning apparatus 100. The operating unit 112 is realized by, for example, a keyboard and a mouse that serve as the input device. The operating unit 112 outputs an operation serving as operation information, which has been input by the user, to the control unit 130. The operating unit 112 may be realized by a touch panel serving as the input device, and the display device of the display unit 111 and the input device of the operating unit 112 may be integrated together.

The storage unit 120 is realized by, for example: a semiconductor memory element, such as a random access memory (RAM) or a flash memory; or a storage device, such as a hard disk or an optical disk. The storage unit 120 has a training data storage unit 121, an extended graph data storage unit 122, and a discriminant model storage unit 123. Further, the storage unit 120 stores therein information used in processing by the control unit 130.

The training data storage unit 121 stores therein, for example, training data to be subjected to learning, which have been input via the communication unit 110. In the training data storage unit 121, for example, graph data to be subjected to learning are stored, the graph data corresponding to a graph representing a structure of a chemical compound and serving as the training data.

The extended graph data storage unit 122 stores therein extended graph data having, added to the training data, a graph formed of wild card nodes corresponding to the graph of the training data. By use of FIG. 5 and FIG. 6, an extended graph and a matrix corresponding to the extended graph, that is, extended graph data, will be described.

Figure 5:
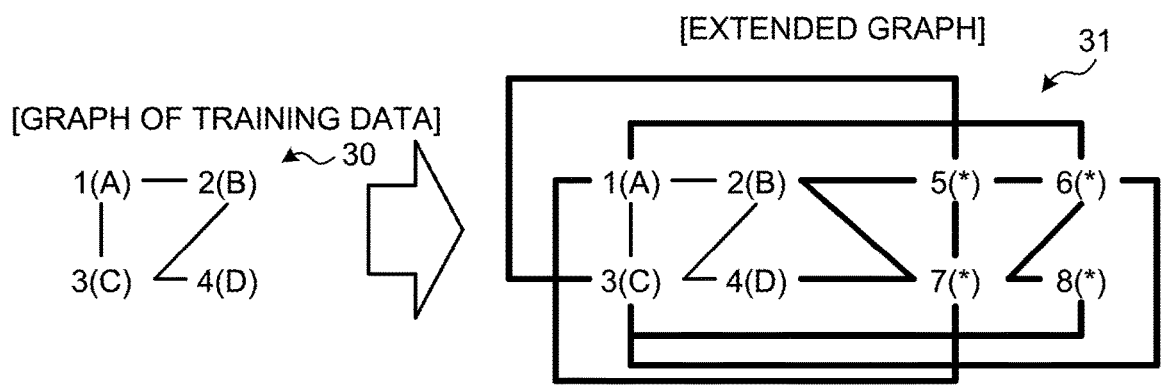
FIG. 5 is a diagram illustrating an example of an extended graph.

FIG. 5 is a diagram illustrating an example of an extended graph. As illustrated in FIG. 5, a graph 30 of training data has labels, "A to D", correspondingly to nodes, "1 to 4". In an extended graph 31, wild card nodes, "5 to 8", having a single label, "*", and corresponding to the nodes, "1 to 4", have been added to the graph 30. Further, in the extended graph 31, connective relations between the added wild card nodes and between the nodes of the graph 30 of the training data and the wild card nodes are set by joining between them with edges correspondingly to the graph 30 of the training data. For example, the node, "1", is connected to the nodes, "2 and 3", and thus is connected also to the wild card nodes, "6 and 7", corresponding to the nodes, "2 and 3". That is, upon extraction of a partial graph structure, the corresponding wild card nodes are selectable from the extended graph 31, instead of the nodes in the graph 30 of the training data having the specific labels.

Figure 6:
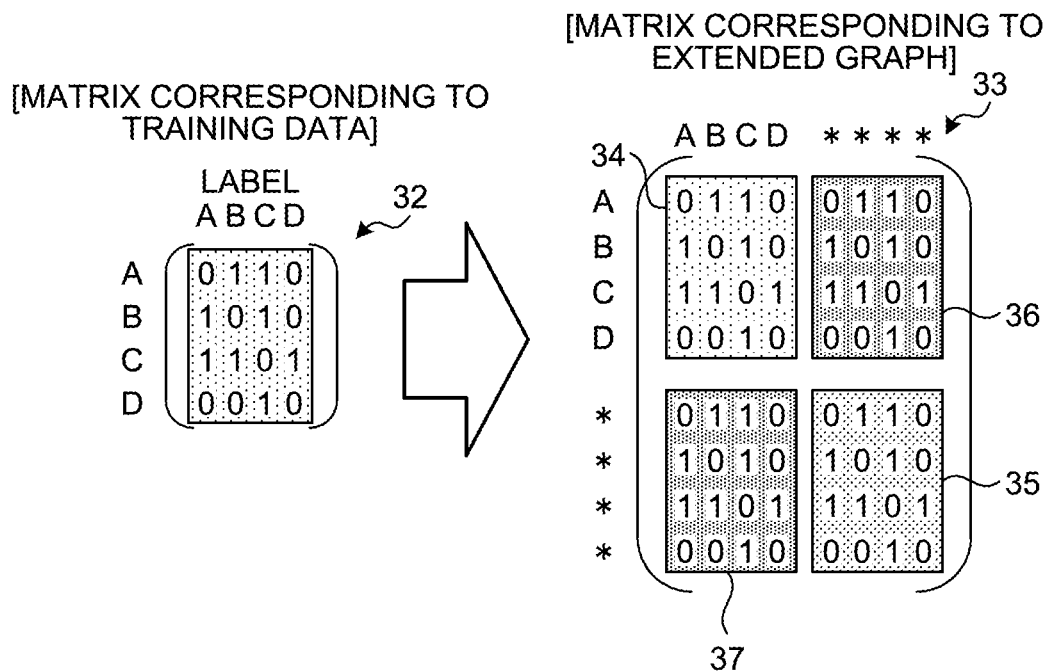
FIG. 6 is a diagram illustrating an example of a matrix corresponding to the extended graph.

FIG. 6 is a diagram illustrating an example of a matrix corresponding to the extended graph. A matrix 32 illustrated in FIG. 6 is a matrix corresponding to the graph 30 of the training data in FIG. 5. Further, a matrix 33 is a matrix corresponding to the extended graph 31 in FIG. 5. The matrix 33 is generated by addition of the matrices 32 vertically and horizontally to the matrix 32. That is, the matrix 33 has a matrix 34 corresponding to the matrix 32, a matrix 35 representing connective information between the wild card nodes of the extended graph 31, and matrices 36 and 37 representing connective information between nodes of the graph 30 and the extended graph 31. The extended graph data storage unit 122 stores therein, for example, the matrix 33 corresponding to the extended graph 31 and serving as extended graph data. If the graph 30 has a node not serving as a wild card, a wild car node corresponding to that node is not set. That is, any row and column corresponding to a wild card node that is not set are deleted from the matrices 35 to 37.

The discriminant model storage unit 123 illustrated in FIG. 1 stores therein a discriminant model resulting from deep learning of extended graph data. The discriminant model is also called a learning model, and stores therein, for example, various parameters (weight coefficients) of a neural network, and a method of tensor decomposition.

The control unit 130 is realized by, for example, a program being executed by a central processing unit (CPU) or a micro processing unit (MPU), with a RAM being a work area, the program having been stored in an internal storage device. Further, the control unit 130 may be realized by, for example, an integrated circuit, such as an application specific integrated circuit (ASIC) or a field programmable gate array (FPGA). The control unit 130 has an obtaining unit 131, a generating unit 132, a learning unit 133, and a discrimination unit 134, and realizes or executes functions and actions of information processing described below. An internal configuration of the control unit 130 is not limited to the configuration illustrated in FIG. 1, and may be any other configuration that performs the information processing described later.

The obtaining unit 131 receives and obtains training data for learning, from a terminal of an administrator, via the communication unit 110, for example. The obtaining unit 131 obtains, for example, the graph 30 illustrated in FIG. 5 and the matrix 32 corresponding to the graph 30. If the training data are of a graph, the obtaining unit 131 converts the training data into a corresponding incidence matrix. The obtaining unit 131 stores the obtained matrix (incidence matrix) or the converted incidence matrix, as the training data, into the training data storage unit 121. When the obtaining unit 131 has stored the training data into the training data storage unit 121, the obtaining unit 131 outputs a generation instruction to the generating unit 132.

When the generation instruction has been input from the obtaining unit 131, the generating unit 132 refers to the training data storage unit 121, and generates, based on the training data, extended graph data. For example, based on the matrix 32 illustrated in FIG. 6 corresponding to the training data, the generating unit 132 generates the matrix 33 corresponding to the extended graph data by adding the matrices 32 vertically and horizontally to the matrix 32. That is, if the training data are formed of n nodes (node numbers: 1 ton; and labels: L1 to Ln), the generating unit 132 generates an incidence matrix between 2n nodes by newly adding n nodes (node numbers: n+1 to 2n; and each label: *). The generating unit 132 stores the generated extended graph data into the extended graph data storage unit 122. When the generating unit 132 has stored the extended graph data into the extended graph data storage unit 122, the generating unit 132 outputs a learning instruction to the learning unit 133.

In other words, the generating unit 132 generates, from graph data to be subjected to learning, extended graph data where some of nodes included in the graph data have a value of the nodes and a value corresponding to presence or absence of an indefinite element at the nodes. That is, the generating unit 132 generates extended graph data by adding wild card nodes to graph data, the wild card nodes corresponding to nodes of the graph data and having labels that are indefinite elements.

When the learning instruction has been input from the generating unit 132, the learning unit 133 refers to the extended graph data storage unit 122, and generates or updates a discriminant model by learning with the extended graph data. That is, the learning unit 133 generates a core tensor (a partial graph structure) by performing tensor decomposition of the extended graph data. The learning unit 133 inputs the generated core tensor into a neural network, and obtains an output. The learning unit 133 performs learning such that error in output values is decreased, and learns parameters of the tensor decomposition such that the determination accuracy is increased. The tensor decomposition has freedom, and examples of the parameters of the tensor decomposition include a combination of a decomposition model, constraints, and optimization algorithm. Examples of the decomposition model include canonical polyadic (CP) decomposition, and Tucker decomposition. Examples of the constraints include orthogonality constraints, sparse constraints, smooth constraints, and non-negative constraints. Examples of the optimization algorithm include the alternating least squares (ALS) method, the higher order singular value decomposition (HOSVD), and the higher order orthogonal iteration of tensors (HOOI). In Deep Tensor, tensor decomposition is performed under a constraint that "the determination accuracy becomes high".

Thereafter, if learning has been executed for a predetermined number of times, or if the error has become less than a predetermined value, the learning unit 133 finishes learning, and stores various parameters and a method of the tensor decomposition as a discriminant model, into the discriminant model storage unit 123. As the neural network, any of various neural networks, such as a recurrent neural network (RNN), may be used. Further, any of various methods, such as the back propagation method, may be used as a learning method.

Figure 7:
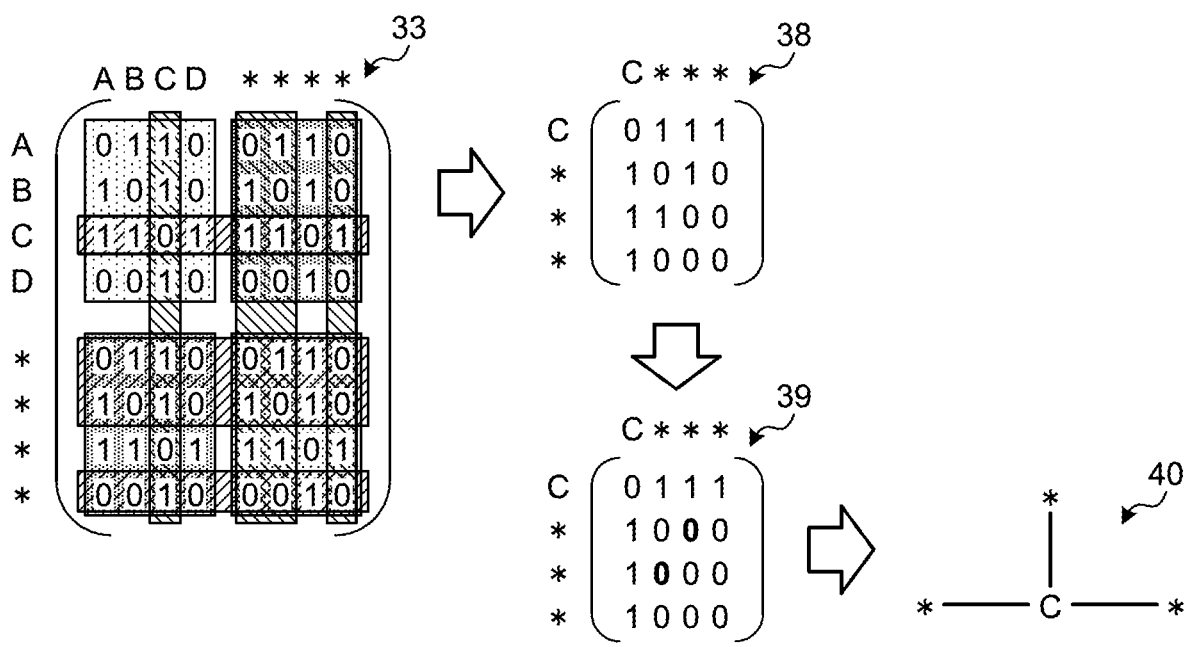
FIG. 7 is a diagram illustrating an example of extraction of a partial graph structure from extended graph data.

By use of FIG. 7, extraction of a partial graph structure will now be described. FIG. 7 is a diagram illustrating an example of extraction of a partial graph structure from extended graph data. As illustrated in FIG. 7, by combining together calculation for exchange between specific rows and between specific columns, calculation for extraction of specific rows and columns, and calculation for substitution of a non-zero element in an incidence matrix with a zero; for the matrix 33, a matrix 38 of a partial graph structure is extracted. In the example of FIG. 7, the learning unit 133 generates the matrix 38 by extracting, from the matrix 33, rows and columns related to the label, "C", and the label, "*" of the wild cards corresponding to the labels, "A, B, and D". These are rows and columns corresponding to the nodes, "3, 5, 6, and 8", in the extended graph 31 in FIG. 5. Subsequently, the learning unit 133 generates a matrix 39 by substitution of values among the nodes, "5 and 6", of the matrix 38 with zeros. A graph 40 is a partial graph structure corresponding to the matrix 39. The graph 40 is a graph structure having the label, "C", and the label,"*". Therefore, the learning unit 133 is able to learn a discriminant rule including an indefinite element by learning the matrix 39 corresponding to the graph 40. That is, the learning apparatus 100 is able to learn a true discriminant rule that has been generalized.

In other words, the learning unit 133 performs tensor decomposition of the generated extended graph data serving as input tensor data, performs deep learning with a neural network by input of the decomposed data into the neural network upon deep learning, and learns a method of the tensor decomposition.

After the learning of the discriminant model, the discrimination unit 134 illustrated in FIG. 1 obtains new data, and outputs a discrimination result resulting from discrimination of the new data by use of the discriminant model. The discrimination unit 134 receives and obtains new data to be discriminated, from a terminal of an administrator, via the communication unit 110, for example. Similarly to the generating unit 132 at the time of learning, the discrimination unit 134 generates, based on the obtained new data, extended graph data.

The discrimination unit 134 discriminates the generated extended graph data by referring to the discriminant model storage unit 123 and using the discriminant model. That is, the discrimination unit 134 constructs a neural network having the various parameters of the discriminant model set therein, and sets a method of the tensor decomposition. The discrimination unit 134 performs tensor decomposition of the generated extended graph data, inputs the decomposed data into the neural network, and obtains a discrimination result. The discrimination unit 134 outputs and displays the obtained discrimination result on the display unit 111, and outputs and stores the obtained discrimination result into the storage unit 120.

A specific example will now be described by use of FIG. 8. In this specific example, it is supposed that there is a task that "whether a certain chemical compound is acidic is desired to be determined". In this case, an incidence matrix having identity representing a structure of a chemical compound serves as training data. Further, an objective variable is "1" when the chemical compound is acidic, and "0" when the chemical compound is not acidic.

Figure 8:
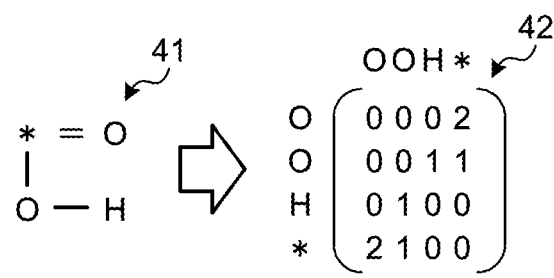
FIG. 8 is a diagram illustrating an example of a partial graph structure including a wild card.

FIG. 8 is a diagram illustrating an example of a partial graph structure including a wild card. A graph 41 illustrated in FIG. 8 is an example of a chemical compound having a wild card in a part of its structural formula. A matrix 42 is an incidence matrix corresponding to the graph 41. In the matrix 42, a component, "1", represents a single bond, and a component, "2", represents a double bond. That is, when graph data represent a structure of a chemical compound, the learning apparatus 100 generates extended graph data having values corresponding to bond orders between atoms of the chemical compound. It is now supposed that a discriminant rule that is learnt defines that a chemical compound including the partial graph structure represented by the graph 41 is acidic.

If a wild card is unable to be used in this example, learning will be performed by assignment of a specific chemical element in the training data to the node having the label, "*". Examples of chemical elements assigned to the label, "*", include: C (carboxylic acid), S (sulfonic acid), P (phosphoric acid), As (arsenic acid), I (iodic acid), and B (metaboric acid); and acidity is demonstrated with various chemical elements. A chemical compound including the partial graph structure represented by the graph 41 is called an oxo acid, and regardless of the chemical element of the label, "*", the chemical compound is known to be acidic due to the two oxygens connected to that chemical element. Therefore, if a wild card is unable to be used, all of chemical elements that are able to form an oxo acid will need to be included in the training data. In contrast, according to this embodiment, by learning with the matrix 42 serving as an input, the matrix 42 corresponding to the graph 41 including a wild card node, a partial graph structure representing such a chemical property will be able to be learnt. That is, the training data may include not all of chemical elements that are able to form an oxo acid.

Figure 9:
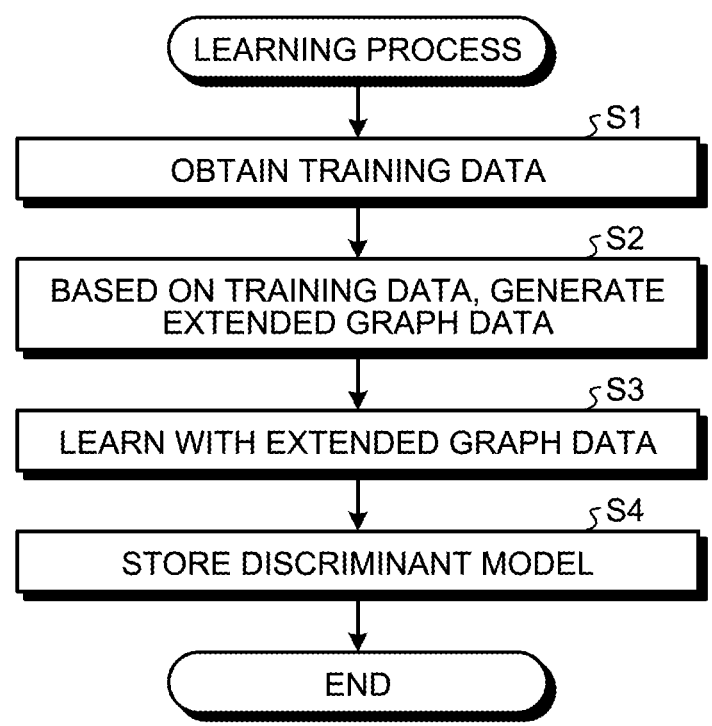
FIG. 9 is a flow chart illustrating an example of a learning process according to the embodiment.

Next, operation of the learning apparatus 100 according to the embodiment will be described. Firstly, a learning process of learning a discriminant model will be described. FIG. 9 is a flow chart illustrating an example of a learning process according to the embodiment.

The obtaining unit 131 receives and obtains training data for learning, from, for example, a terminal of an administrator (Step S1). The obtaining unit 131 stores the obtained training data into the training data storage unit 121. When the obtaining unit 131 has stored the training data into the training data storage unit 121, the obtaining unit 131 outputs a generation instruction to the generating unit 132.

When the generation instruction has been input from the obtaining unit 131, the generating unit 132 refers to the training data storage unit 121, and generates, based on the training data, extended graph data (Step S2). The generating unit 132 stores the generated extended graph data into the extended graph data storage unit 122. When the generating unit 132 has stored the extended graph data into the extended graph data storage unit 122, the generating unit 132 outputs a learning instruction to the learning unit 133.

When the learning instruction has been input from the generating unit 132, the learning unit 133 refers to the extended graph data storage unit 122, and performs learning with the extended graph data (Step S3). If learning has been executed for a predetermined number of times, or if the error has become less than a predetermined value, the learning unit 133 finishes learning, and stores various parameters and a method of the tensor decomposition as a discriminant model, into the discriminant model storage unit 123 (Step S4). Thereby, the learning apparatus 100 enables improvement in the discrimination accuracy of machine learning for a graph including an indefinite element in the discriminant rule.

Figure 10:
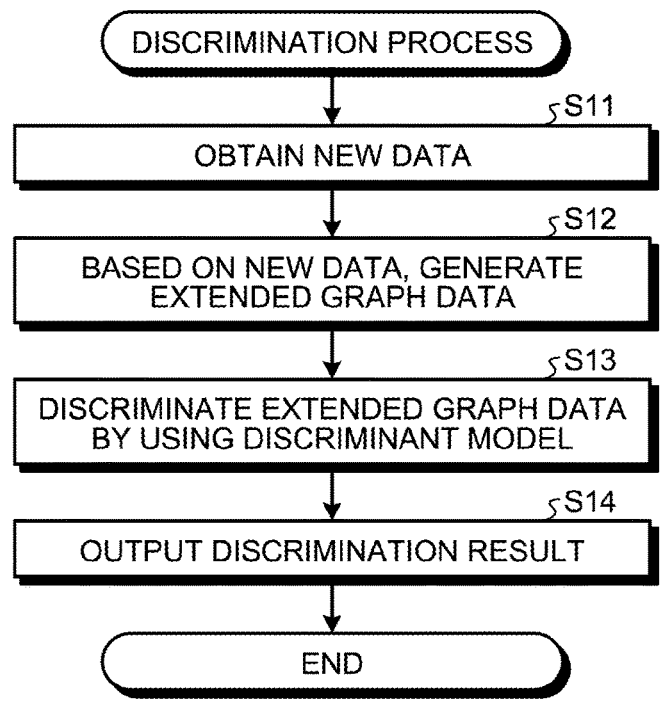
FIG. 10 is a flow chart illustrating an example of a discrimination process according to the embodiment.

Next, a discrimination process for discrimination of new data will be described. FIG. 10 is a flow chart illustrating an example of a discrimination process according to the embodiment.

The discrimination unit 134 receives and obtains new data to be discriminated, from, for example, a terminal of an administrator (Step S11). Based on the obtained new data, the discrimination unit 134 generates extended graph data (Step S12). The discrimination unit 134 discriminates the generated extended graph data by referring to the discriminant model storage unit 123 and using the discriminant model (Step S13). The discrimination unit 134 outputs and displays a discrimination result of the discriminant model on, for example, the display unit 111 (Step S14). Thereby, the learning apparatus 100 is able to discriminate data of a graph structure having a partial graph structure including an arbitrary label.

That is, since the learning apparatus 100 is able to learn a partial graph structure including a wild card node, improvement in the discrimination performance for new data is able to be expected. For example, it is now supposed that a true determination rule defines that "a positive example includes a partial graph structure X including a wild card node". As illustrated in FIG. 4, in conventional Deep Tensor, in the graph processing mode with labels, a positive example including the partial graph structure X but not present in the training data will be erroneously determined as a negative example. Further, in the graph processing mode without labels, a negative example will be erroneously determined as a positive example, the negative example including a partial graph structure, which corresponds to the partial graph structure X, and results from substitution of a node that can only have a specific label, with a node having a label other than the specific label. In contrast, the learning apparatus 100 according to the embodiment is able to make correct determination for both of the above described erroneous determinations in the two modes.

The learning apparatus 100 thus generates, from graph data to be subjected to learning, extended graph data where at least some of nodes included in the graph data have a value of the nodes and a value corresponding to presence or absence of an indefinite element at the nodes. Further, the learning apparatus 100 performs tensor decomposition of the generated extended graph data serving as input tensor data, performs deep learning with a neural network by input of the decomposed data into the neural network upon deep learning, and learns a method of the tensor decomposition. As a result, the learning apparatus 100 enables improvement in the discrimination accuracy of machine learning for a graph including an indefinite element in the discriminant rule.

Further, the learning apparatus 100 generates extended graph data by adding wild card nodes to graph data, the wild card nodes having indefinite elements serving as labels of nodes of the graph data. As a result, the learning apparatus 100 is able to learn a discriminant rule including an indefinite element.

Further, when graph data represent a structure of a chemical compound, the learning apparatus 100 generates extended graph data having values corresponding to bond orders between chemical atoms of the chemical compound. As a result, the learning apparatus 100 is able to learn a structure of a chemical compound.

The RNN has been mentioned as an example of the neural network according to the embodiment, but the neural network is not limited to the RNN. Any of various neural networks, for example, a convolutional neural network (CNN), may be used. Further, any of various known techniques other than the back propagation, may be adopted as a learning technique. Furthermore, the neural network has a multistage structure formed of, for example, an input layer, an intermediate layer (a hidden layer), and an output layer, and each layer has a structure where plural nodes are joined by edges. Each layer has a function called an "activation function"; the edges have "weight"; and a value of each node is calculated from a value of a node of a previous layer, a value of weight of an edge connected to the node, and an activation function that the layer has. Any of various known methods may be adopted as a method for the calculation. Moreover, any of various techniques, such as the support vector machine (SVM) technique, may be used for machine learning, other than the neural network.

Further, the components of each unit illustrated in the drawings may be not configured physically as illustrated in the drawings. That is, specific modes of separation and integration of the units are not limited to those illustrated in the drawings, and all or a part of the units may be functionally or physically separated or integrated in arbitrary units according to various loads and use situations. For example, the obtaining unit 131 and the generating unit 132 may be integrated together. Furthermore, the sequences of steps in the processes illustrated in the drawings are not limited to those described above, and any of the steps may be performed simultaneously, or performed in a different sequence, as long as no contradictions in the processing content arise therefrom.

Further, all or any part of the various processing functions performed in each device may be executed on a CPU (or a microcomputer, such as an MPU, or a microcontroller unit (MCU)). Furthermore, needless to say, all or any part of the various processing functions may be executed on a program analyzed and executed by a CPU (or a microcomputer, such as an MPU or MCU), or on hardware by wired logic.

Figure 11:
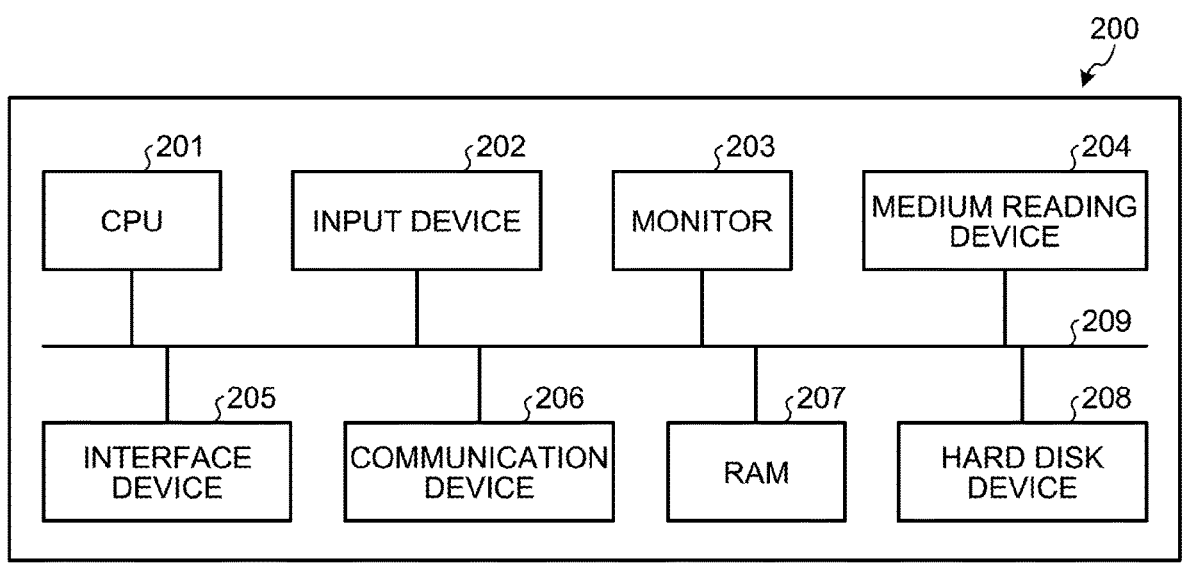
FIG. 11 is a diagram illustrating an example of a computer that executes a learning program.

The various processes described with respect to the above embodiment may be realized by a program being executed by a computer, the program having been prepared beforehand. Thus, hereinafter, an example of a computer that executes a program having the same functions as those of the above described embodiment will be described. FIG. 11 is a diagram illustrating an example of a computer that executes a learning program.

As illustrated in FIG. 11, a computer 200 has a CPU 201 that executes various kinds of calculation processing, an input device 202 that receives input of data, and a monitor 203. Further, the computer 200 has a medium reading device 204 that reads a program from a storage medium, an interface device 205 for connection to various devices, and a communication device 206 for wired or wireless connection to another information processing apparatus. Furthermore, the computer 200 has a RAM 207 that temporarily stores therein various kinds of information, and a hard disk device 208. Moreover, these devices 201 to 208 are connected to a bus 209.

The hard disk device 208 has a learning program stored therein, the learning program having the same functions as those of the processing units including the obtaining unit 131, the generating unit 132, the learning unit 133, and the discrimination unit 134, which are illustrated in FIG. 1. Further, the hard disk device 208 stores therein various data for realizing the training data storage unit 121, the extended graph data storage unit 122, the discriminant model storage unit 123, and the learning program. The input device 202 receives input of various kinds of information, such as operation information, from, for example, an administrator of the computer 200. The monitor 203 displays thereon various screens, such as display screens, for the administrator of the computer 200, for example. A printing device, for example, is connected to the interface device 205. The communication device 206, for example, has the same functions as those of the communication unit 110 illustrated in FIG. 1, is connected to a network not illustrated in the drawings, and exchanges various kinds of information with the other information processing apparatus.

The CPU 201 performs various kinds of processing by reading each program stored in the hard disk device 208 and decompressing and executing the program on the RAM 207. Further, these programs are able to cause the computer 200 to function as the obtaining unit 131, the generating unit 132, the learning unit 133, and the discrimination unit 134 that are illustrated in FIG. 1.

The learning program may be not stored in the hard disk device 208. For example, a program stored in a storage medium readable by the computer 200 may be read and executed by the computer 200. The storage medium readable by the computer 200 corresponds to, for example: a portable recording medium, such as a CD-ROM, a digital versatile disc (DVD), or a universal serial bus (USB) memory; a semiconductor memory, such as a flash memory; or a hard disk drive. Further, the learning program may be stored beforehand in a device connected to a public line, the Internet, or a LAN; and the computer 200 may read and execute the learning program therefrom.

Discrimination accuracy of machine learning for a graph including an indefinite element in a discriminant rule thereof is able to be improved.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiment of the present invention has been described in detail, it should be understood that the various changes, substitutions, and alterations could be made hereto without departing from the spirit and scope of the invention.

What is claimed is:

1. A non-transitory computer-readable recording medium having stored therein a learning program that causes a computer to execute a machine learning process for graph data, the machine learning process comprising:

generating, from graph data to be subjected to learning, extended graph data where at least some of nodes included in the graph data have a first value of the node and a second value of a wild card node, which is a node having an indefinite element, the graph data including nodes that represent chemical elements and edges that represent bonds between the chemical elements, the first value of the node being a node label;

obtaining input tensor data, performing deep learning with a neural network by inputting the input tensor data into the neural network upon deep learning, and learning a method of the tensor decomposition; and outputting a discrimination result of data of a graph structure having a partial graph structure including an arbitrary label, wherein when the graph data represent a structure of a chemical compound, the generating includes generating the extended graph data having values corresponding to bond orders between atoms of the chemical compound, wherein an incidence matrix having identity representing a structure of a chemical compound serves as the graph data to be subjected to learning, and the learning includes learning with the incidence matrix serving as an input, the incidence matrix corresponding to the graph data including the wild card node.

2. A learning method implemented by a computer that executes a machine learning process for graph data, the learning method comprising:

generating, from graph data to be subjected to learning, extended graph data where at least some of nodes included in the graph data have a first value of the node and a second value of a wild card node, which is a node having an indefinite element, using a processor, the graph data including nodes that represent chemical elements and edges that represent bonds between the chemical elements, the first value of the node being a node label;

obtaining input tensor data by performing tensor decomposition of the generated extended graph data, performing deep learning with a neural network by inputting the input tensor data into the neural network upon deep learning, and learning a method of the tensor decomposition, using the processor; and outputting a discrimination result of data of a graph structure having a partial graph structure including an arbitrary label, wherein when the graph data represent a structure of a chemical compound, the generating includes generating the extended graph data having values corresponding to bond orders between atoms of the chemical compound, wherein an incidence matrix having identity representing a structure of a chemical compound serves as the graph data to be subjected to learning, and the learning includes learning with the incidence matrix serving as an input, the incidence matrix corresponding to the graph data including the wild card node.

3. A learning apparatus that performs machine learning for graph data, the learning apparatus comprising:

a memory; and a processor coupled to the memory, wherein the processor executes a process comprising:

generating, from graph data to be subjected to learning, extended graph data where at least some of nodes included in the graph data have a first value of the node and a second value of a wild card node, which is a node having an indefinite element, the graph data including nodes that represent chemical elements and edges that represent bonds between the chemical elements, the first value of the node being a node label;

obtaining input tensor data by performing tensor decomposition of the generated extended graph data, performing deep learning with a neural network by inputting the input tensor data into the neural network upon deep learning, and learning a method of the tensor decomposition; and outputting a discrimination result of data of a graph structure having a partial graph structure including an arbitrary label, wherein when the graph data represent a structure of a chemical compound, the generating includes generating the extended graph data having values corresponding to bond orders between atoms of the chemical compound, wherein an incidence matrix having identity representing a structure of a chemical compound serves as the graph data to be subjected to learning, and the learning includes learning with the incidence matrix serving as an input, the incidence matrix corresponding to the graph data including the wild card node.

* * * * *